(12) United States Patent
Hulteberg et al.

(10) Patent No.: US 8,692,028 B2
(45) Date of Patent: Apr. 8, 2014

(54) METHOD FOR HYDROGENATING 1,2-UNSATURATED CARBONYLIC COMPOUNDS

(75) Inventors: Christian Hulteberg, Malmö (SE); Jan Brandin, Malmö (SE)

(73) Assignee: BioFuel-Solution i Malmo AB, Limhamn (SE)

( * ) Notice: Subject to any disclaimer, the term of this patent is extended or adjusted under 35 U.S.C. 154(b) by 26 days.

(21) Appl. No.: 13/517,119

(22) PCT Filed: Dec. 21, 2010

(86) PCT No.: PCT/EP2010/070371
§ 371 (c)(1),
(2), (4) Date: Sep. 6, 2012

(87) PCT Pub. No.: WO2011/076787
PCT Pub. Date: Jun. 30, 2011

(65) Prior Publication Data
US 2012/0323043 A1    Dec. 20, 2012

Related U.S. Application Data

(60) Provisional application No. 61/282,158, filed on Dec. 23, 2009.

(51) Int. Cl.
*C07C 45/62* (2006.01)
(52) U.S. Cl.
USPC ....................................................... 568/462
(58) Field of Classification Search
USPC ....................................................... 568/462
See application file for complete search history.

(56) References Cited

FOREIGN PATENT DOCUMENTS

EP    0 822 173 A1    2/1998

OTHER PUBLICATIONS

International Search Report for corresponding International Application No. PCT/EP2010/070371 mailed Mar. 29, 2011.
Written Opinion of the International Searching Authority for corresponding International Application No. PCT/EP2010/070371 mailed Mar. 29, 2011.
Nitta et al., "Activation-temperature dependence in enantioselective hydrogenation of unsaturated carboxylic acids over cinchonidine-modified Pd/C catalysts", Journal of Catalysis, vol. 236, 2005, pp. 164-167.
Hirschl et al., "Adsorption of unsaturated aledhydes on the (111) surface of a Pt-Fe alloy catalyst from first principles", Journal of Catalysis, vol. 217, 2003, pp. 354-366.
Maki-Arvela et al., "Chemoselective hydrogenation of carbonyl compounds over heterogeneous catalysts", Applied Catalysis A: General, vol. 292, 2006, pp. 1-49.
Claus, "Selective hydrogenation of α,β-unsaturated aldehydes and other C=O and C=C bonds containing compounds", Topics in Catalysis 5, 1998, pp. 51-62.
Rase, H.F. Handbook of Commercial Catalysts, Boca Raton, CRC Press LLC, 2000. pp. 168-169.

*Primary Examiner* — Sikarl Witherspoon
(74) *Attorney, Agent, or Firm* — Renner, Otto, Boisselle & Sklar, LLP

(57) ABSTRACT

Disclosed is a method of hydrogenating an 1,2-unsaturated carbonylic compound to obtain the corresponding saturated carbonylic compound in the presence of a palladium catalyst with heterogeneous distribution of palladium.

19 Claims, 3 Drawing Sheets

METHOD FOR HYDROGENATING 1,2-UNSATURATED CARBONYLIC COMPOUNDS

This application is a national phase of International Application No. PCT/EP2010/070371 filed Dec. 21, 2010 and published in the English language, which claims priority to Application No. U.S. 61/282,158 filed Dec. 23, 2009.

FIELD OF THE INVENTION

The present invention relates to hydrogenation of 1,2-unsaturated carbonylic compounds, such as 1,2-unsaturated aldehydes, to the corresponding saturated carbonylic compounds, such as saturated aldehydes, by use of a palladium catalyst

BACKGROUND

Catalytic hydrogenations are employed to add hydrogen over double and triple bonds. As an example, catalytic hydrogenation of vegetable oils is employed to change the physical properties, such as the melting point, of vegetable oils to obtain semi-solid fat suitable for use in the food industry.

Catalytic hydrogenations are also commonly used in the chemical industries, such as in petrochemical processes. Typically, expensive noble metals, such as platinum and palladium, are used as catalysts in catalytic hydrogenations. Different catalyst may display different selectivity towards different types of double and triple bonds. Further, the catalyst used is often supported by a carrier, such as carbon or alumina. Typically, the carrier is porous and the catalyst is distributed homogenously throughout the carrier, i.e. at both external and internal surfaces, to take advantage of the large surface area of the porous carrier.

The saturated aldehyde propionaldehyde, being an interesting building block in the petrochemical industry, may be obtained by selective gas phase hydrogenation of the corresponding 1,2-unsaturated aldehyde, i.e. acrolein.

It is well known within the art that palladium (Pd) has the ability to selectively catalyze the hydrogenation of 1,2-unsaturated aldehydes, such as acrolein and crotonaldehyde, to their corresponding saturated aldehydes, i.e. propionaldehyde and butyraldehyde (cf. Rase, H. F. Handbook of Commercial Catalysts. Boca Raton, CRC Press LLC, 2000. pp. 168-169; ISBN 0-8493-9417-1). Commonly employed catalysts for this reaction are Pd-on-carbon 5% in the slurry phase and 0.5% Pd on $Al_2O_3$.

As most catalysts within the art has been developed to produce the unsaturated alcohol (Claus, P. 1998, Topics in Catalysis, Vol. 5, pp. 51-62, P. Maki-Arvela, J. Hajek, T. Salmi, D. Y. Murzin. 2005, Appl. Catal. A. Gen., Vol. 292, pp. 1-49, and R. Hirschl, F. Delbecq, P. Sautet, J. Hafner. 2003, Vol. 217, pp. 354-366), a low cost selective catalyst for the production of the saturated aldehydes would be of interest.

Further, gas phase hydrogenation of for example acrolein in the presence of Pd on $Al_2O_3$ is not completely selective towards propionaldehyde, and ethene, as well as ethane, is formed, in addition to propionaldehyde. Thus, a more selective process would be desired.

Thus, there is need within the art for an method for producing saturated aldehydes, such as propionaldehyde, from 1,2-unsaturated aldehydes, such as acrolein, overcoming the above-mentioned deficiencies.

SUMMARY

Consequently, the present invention seeks to mitigate, alleviate, eliminate or circumvent one or more of the above-identified deficiencies in the art and disadvantages singly or in any combination by providing a method of hydrogenating a carbon-carbon double bond conjugated with a carbonyl carbon in an 1,2-unsaturated carbonylic compound in gas phase. The method comprises the step of:

passing a gaseous stream comprising an 1,2-unsaturated carbonylic compound to be hydrogenated and hydrogen over a palladium catalyst comprising a carrier and palladium, wherein said catalyst has a heterogeneous distribution of palladium, palladium being concentrated to the outermost surface of the catalyst, which outermost surface is being exposed to the surrounding;

wherein the temperature over said catalyst is 120 to 200° C., such as 170 to 190° C., and the pressure over said catalyst is at least 0.1 MPa, such as 0.1 to 10 MPa, or 1 to 5 MPa.

Further, the present invention also seeks to mitigate, alleviate, eliminate or circumvent one or more of the above-identified deficiencies in the art and disadvantages singly or in any combination by using a palladium catalyst comprising a carrier and palladium, wherein the catalyst has a heterogeneous distribution of palladium, palladium being concentrated to the outermost surface of the catalyst, which outermost surface is being exposed to the surrounding, in the gas phase hydrogenation of a carbon-carbon double bond conjugated with a carbonyl carbon in an 1,2-unsaturated carbonylic compound.

At least 95 wt %, such as at least 97.5, 99.0, or 99.5 wt %, of the palladium in the catalyst, may be present at or within 1 mm, such as within 500 or 300 µm, of the outermost surface of said catalyst. The catalyst may comprise between 1 wt % and 0.01 wt % palladium; and the carrier may essentially consist of alumina ($Al_2O_3$).

Further, the 1,2-unsaturated carbonylic compound may be a compound according to structural formula (I),

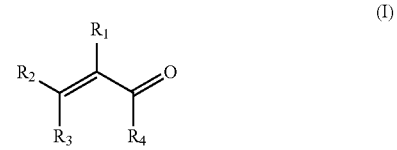

(I)

wherein $R_1$, $R_2$ and $R_3$, independently of each other, are selected from the group consisting of hydrogen and $C_{1-4}$ alkyl; and $R_4$ are selected from the group consisting of hydrogen, $C_{1-4}$ alkyl, OH, $OC_{1-4}$ alkyl, and $NR_5R_6$, wherein $R_5$ and $R_6$, independently of each other, are selected from the group consisting of hydrogen and $C_{1-4}$ alkyl. Examples of 1,2-unsaturated carbonylic compounds are acrolein and crotonaldehyde.

Further advantageous features of the invention are defined in the dependent claims. In addition, advantageous features of the invention are elaborated in embodiments disclosed herein.

EMBODIMENTS

During experimental work it was unexpectedly found that the activity of Pd on $Al_2O_3$, in catalyzing gas phase hydrogenation of 1,2-unsaturated aldehydes is proportional to the outer surface of the catalyst pellet, not the overall surface area, including the inner areas of the catalyst as well. As the overall inner area of the catalyst is significantly larger than the outer area, this strongly suggests that the reaction, i.e. the gas phase hydrogenation of 1,2-unsaturated aldehydes to the corresponding saturated aldehydes, is fast by nature. Indeed, the reaction has been found to be fast even at as low temperatures as 100 to 150° C. and at as low pressures as 1 to 10 bar.

It was thus envisaged that commonly employed catalyst with a homogenous distribution of palladium throughout the catalyst may be re-placed with a catalyst having a heterogeneous distribution of palladium in the catalyst. A catalyst having a heterogeneous distribution of palladium in the catalyst may be a catalyst comprising palladium and a carrier, wherein the palladium is concentrated to the outer surface of the catalyst, being exposed to the surrounding. Catalysts with a homogenous distribution of palladium throughout the catalyst may also be denoted homogeneously impregnated catalysts. In such catalyst with a homogenous distribution of palladium throughout the catalyst, palladium has been deposited at the inner as well as the outer surfaces of the carrier. By only depositing palladium at the outer surfaces of the carrier, a catalyst with heterogeneous distribution of palladium in the catalyst may be obtained.

Catalysts with heterogeneous distribution of the active phase, eg. palladium, wherein the active phase is concentrated to the outermost or exterior surfaces of the catalyst, being exposed to the surrounding, are known within the art and are often denoted egg-shell catalysts [Applied Catalysis A: General 301 (2006) 138-142].

As seen from FIGS. 1 and 2, it was found that use of an egg-shell catalyst (0.18 wt % Pd on $Al_2O_3$) compared to a homogenous catalyst of the art (2 wt % Pd on $Al_2O_3$), in the hydrogenation of acrolein, resulted, not only in comparable, but actually in higher yield of propionaldehyde at a constant outer-surface-area load of palladium. Further, the yield of by-products was lower with the egg-shell catalyst. Hence, similar or even superior results may be obtained with use of significantly less palladium.

Accordingly, an embodiment relates to use of a palladium catalyst comprising a carrier and palladium, wherein the catalyst has a heterogeneous distribution of palladium, palladium being concentrated to the outermost surface of the catalyst, which outermost surface is being exposed to the surrounding, in the gas phase hydrogenation of a carbon-carbon double bond conjugated with a carbonyl carbon in an 1,2-unsaturated carbonylic compound.

Further, another embodiment relates to a method of hydrogenating a carbon-carbon double bond conjugated with a carbonyl carbon in an 1,2-unsaturated carbonylic compounds in gas phase, comprising the step of:

passing a gaseous stream comprising the 1,2-unsaturated carbonylic compound to be hydrogenated and hydrogen over a palladium catalyst comprising a carrier and palladium, wherein the catalyst has a heterogeneous distribution of palladium, palladium being concentrated to the outermost surface of the catalyst, which outermost surface is being exposed to the surrounding, wherein the temperature over said catalyst is 120 to 200° C. and the pressure over said catalyst is at least 0.1 MPa.

A type of palladium catalysts comprising a carrier and palladium, wherein the catalyst has a heterogeneous distribution of palladium are egg-shell catalysts. In such catalysts palladium is concentrated to the outermost surface of the catalyst. The outermost surface of the catalyst is the surface being exposed to the surrounding.

In palladium catalysts having homogenous distribution of palladium, palladium is present throughout the catalyst at the outermost surface as well as at inner surfaces. The inner surfaces are typically surfaces of pores within the carrier.

As indicated, the catalysts employed in the hydrogenation of 1,2-unsaturated carbonylic compounds may have a heterogeneous distribution of palladium. In a catalyst with heterogeneous distribution of palladium, palladium may be concentrated to the outermost surface of the catalyst. According to an embodiment, at least 95 wt %, such as at least 97.5, 99.0, or 99.5 wt %, of the palladium in the catalyst, may be present at or within 1 mm, such as within 500 or 300 µm, of the outermost surface of the catalyst having heterogeneous distribution of palladium.

Further, in a catalyst, having heterogeneous distribution of palladium, in form of a particle or particles attached to each other, at least 95 wt %, such as at least 97.5, 99.0 or 99.5 wt %, of the palladium in the catalyst, may be present at the outermost surface of the catalyst, or within a distance from the outermost surface of the catalyst of not more than 1%, such as not more than 0.1 or 0.01%, of the distance between the outermost surface and the center of gravity of the particle.

Although being heterogeneously distributed within the catalyst, the distribution of palladium at the outermost surface of the catalyst may be essentially homogenous.

In a catalyst, having heterogeneous distribution of palladium, wherein the palladium is concentrated to the outermost surface of the catalyst, at least 95.0 wt % of the palladium in the catalyst, such as at least 97.5, 99.0 wt % or substantially all of the palladium in the catalyst, may be concentrated to a skin periphery of the catalyst having a thickness not more than 400 µm.

According to an embodiment, the amount of palladium present in the catalyst may constitute not more than 1 wt %, such as not more than 0.5 or 0.1 wt %, of the catalyst. As a certain amount of palladium may be required to obtain sufficient catalytic activity, the amount of palladium present in the catalyst may be at least 0.01 wt %, such as at least 0.05 or 0.1 wt %.

According to an embodiment, the carrier comprises, such as essentially consists of, alumina ($Al_2O_3$). The carrier may also be or comprise active carbon. The catalyst itself may take various shapes, such as pellets in the form of e.g. spheres and spoked wheels, extrudates, monoliths, and wash-coated wire mesh. Typically, the catalyst is a pellet having a diameter of 2 mm to 10 mm and a BET surface area between 25 and 300 g/m² with macro-, meso- and micro-pores. The catalyst also be extrudates with a cross sectional diameter of 2 mm to 10 mm and similar BET surface area and pore-size distribution may be used According to an embodiment, the catalyst essentially consists of alumina and heterogeneously distributed palladium.

An alumina carrier, being a preferred type of carrier, may be prepared by conventional methods. For example, during the preparation of carrier, alumina powder and water may be kneaded and extruded, then dried at 40 to 120° C., and calcinated at 300 to 600° C. for 4 to 6 hours.

A catalyst with heterogeneous distribution of palladium, wherein palladium is concentrated to the outermost surface of the catalyst, may be obtained by impregnation techniques within the art used to obtain shell catalyst. As an example, the alumina carrier may first be pre-impregnated with a liquid miscible with a salt solution containing palladium. Subsequently, the pre-impregnated alumina carrier may be impregnated with a salt solution containing palladium and the resultant impregnated alumina carrier may be washed, dried, and calcinated at 350 to 500° C. for 2 to 4 hours to obtain a palladium egg-shell catalyst.

Further, although the alumina carrier may be alumina in any form, the γ-form is the preferred form. A commonly used liquid used for pre-impregnating the alumina carrier is de-ionized water.

The temperature at which the hydrogenation is performed may be of importance. At a too low temperature, such as below 100° C., the hydrogenation will to be slow. Further, a too low temperature may imply that a low pressure has to be used to keep the 1,2-unsaturated carbonylic compound in gas phase, thus negatively affecting the mass flow. On the contrary, at a too high temperature, such as above 200° C., the formation of side-products will be too extensive. Accordingly, the hydrogenation of 1,2-unsaturated carbonylic compounds, may typically be performed at a temperature of 120 to 200° C., such as 170 to 190° C.

Further, the hydrogenation may typically be performed at or above atmospheric pressure, i.e. a pressure of at least 0.1 MPa. The pressure may be 0.1 to 10 MPa, such as 1 to 5 MPa.

Hydrogen is consumed in a 1 to 1 molar ratio in the selective hydrogenation of carbon-carbon double bonds conjugated with a carbonyl carbon in an 1,2-unsaturated carbonylic compound. Hence, the molar amount of hydrogen used is typically at least equal to the molar amount of the 1,2-unsaturated carbonylic compound to be hydrogenated. Further, the molar amount of hydrogen may be 1 to 5 times, such as 1 to 2 times, the molar amount of the 1,2-unsaturated carbonylic compound. If an over-stoichiometric ratio of hydrogen is used, the excess of hydrogen may be separated from the product stream. The separated hydrogen may then be recycled.

Although not necessary, the gaseous stream comprising the 1,2-unsaturated carbonylic compound to by be hydrogenated and hydrogen, may further comprise steam. The gaseous stream may be obtained by mixing a gaseous stream comprising steam and an 1,2-unsaturated carbonylic compound with hydrogen. As an example, a gaseous stream comprising steam and an 1,2-unsaturated carbonylic compound, wherein the 1,2-unsaturated carbonylic compound is acrolein, may be obtained by dehydration of aqueous glycerol in gas phase. WO 2010/052208, which hereby is incorporated in its entirety by reference, discloses various aspects of the dehydration of aqueous glycerol to obtain acrolein. Further, also WO 2006/087084 and U.S. Pat. No. 5,387,720, which hereby are incorporated in their entirety by reference, disclose several aspects of the conversion of glycerol in gas phase to acrolein.

As disclosed herein, 1,2-unsaturated carbonylic compounds may be hydrogenated to the corresponding saturated carbonylic compounds by use of a palladium catalyst comprising a carrier and palladium, wherein the catalyst has a heterogeneous distribution of palladium, the palladium being concentrated to the outermost surface of the catalyst, which outermost surface is being exposed to the surrounding.

1,2-unsaturated carbonylic compounds are compounds comprising the following structural element

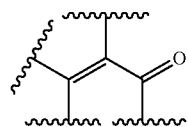

wherein the waved line indicates the point of attachment to the rest of the compound. Preferably, 1,2-unsaturated carbonylic compounds are compounds which may be represented by the following structural formula (I),

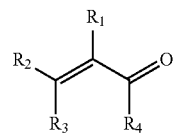

(I)

wherein $R_1$, $R_2$ and $R_3$, independently of each other, are selected from the group consisting of hydrogen and $C_{1-4}$ alkyl; and $R_4$ are selected from the group consisting of hydrogen, i.e. the 1,2-unsaturated carbonylic compound being an aldehyde, $C_{1-4}$ alkyl, i.e. the 1,2-unsaturated carbonylic compound being a ketone, OH, i.e. the 1,2-unsaturated carbonylic compound being a carboxylic acid, $OC_{1-4}$ alkyl, i.e. the 1,2-unsaturated carbonylic compound being a carboxylic acid ester, and $NR_5R_6$, wherein $R_5$ and $R_6$, independently of each other, are selected from the group consisting of hydrogen and $C_{1-4}$ alkyl, i.e. the 1,2-unsaturated carbonylic compound being a amide.

Although the 1,2-unsaturated carbonylic compound also may be a compound, such as an 1,2-unsaturated ketone, a carboxylic acid esters, a carboxylic acid and an amides, it typically is a 1,2-unsaturated aldehyde, such as acrolein or crotonaldehyde.

1,2-unsaturated aldehydes are compounds comprising the following structural element

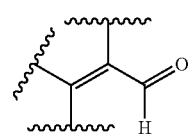 [SMILES: *C(*)=C(*)C=O]

wherein the waved line indicates the point of attachment to the rest of the compound. Preferably, 1,2-unsaturated aldehydes are compounds which may be represented by the following structural formula (II),

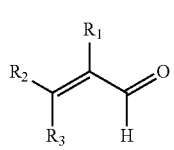

(II)

wherein $R_1$, $R_2$ and $R_3$, independently of each other, are selected from the group consisting of hydrogen and $C_{1-4}$ alkyl. Preferred examples of 1,2-unsaturated aldehydes are acrolein and crotonaldehyde.

A gas phase hydrogenation of a 1,2-unsaturated carbonylic compound, as disclosed herein, may typically be performed in a reactor. The reactor may have an inlet for introducing the gaseous stream comprising the 1,2-unsaturated carbonylic compound and hydrogen. Further, the reactor may have an outlet for effluence of the corresponding saturated carbonylic compound from the reactor. As the hydrogenation is an exothermic reaction, the rector may be provided with cooling means for controlling the temperature within the rector. A preferred type of rector is a flow reactor, such as tubular reactor or a bundle of tubes within a mantle containing a cooling media.

As the hydrogenation of the 1,2-unsaturated carbonylic compound was shown to take place at the outer surface of the catalyst, the conversion rate of the 1,2-unsaturated carbonylic compound is independent of diffusion of the 1,2-unsaturated carbonylic compound to the interior of the catalyst. Hence, a fairly high gas flow rate, such as a gas hour space velocity (GHSV, defined as the gas volumetric flow at normal temperature and pressure (273 K, 1 atm) divided by the catalyst volume) of at least 10 000 h$^{-1}$, may be used.

Although the present invention has been described above with reference to specific embodiments, it is not intended to be limited to the specific form set forth herein. Rather, the invention is limited only by the accompanying claims and, other embodiments than the specific above are equally possible within the scope of these appended claims, e.g. different than those described above.

In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous.

In addition, singular references do not exclude a plurality. The terms "a", "an", "first", "second" etc do not preclude a plurality.

EXPERIMENTAL

The examples given below are only intended to further illustrate the invention and are by no means intended to limit the scope of the invention as defined by the appended claims.

Two sets of catalysts were prepared using incipient wetness preparation methods. Both catalysts had the composition Pd on Al$_2$O$_3$, one homogeneously prepared (2% by weight Pd on Al$_2$O$_3$) and one where the Pd has been concentrated to the outermost surface of the catalyst (0.18% by weight Pd on Al$_2$O$_3$); hereon after denoted "egg-shell" catalyst.

The catalyst with homogenous palladium distribution was obtained by preparing a commercial γ-alumina catalyst pellet with a mean diameter of 5 mm in diameter having a BET surface area of 120 m$^2$/g. The catalyst pellet was impregnated, using the incipient wetness method, with a 1 mol/l aqueous solution of Pd(NO$_3$)$_2$. The resulting preparation was dried at 120° C. for 3 h and then calcined at 500° C. for 3 h yielding a catalyst containing 2 wt % palladium.

Similarly, the egg-shell catalyst was obtained by preparing a commercial γ-alumina catalyst pellet with a mean diameter of 5 mm in diameter having a BET surface area of 120 m$^2$/g. The catalyst pellets were soaked for 30 min in n-undecane, for filling the pore-system of the catalyst with the organic solvent. The catalyst pellets were then dried briefly in an oven at 120° C. for evaporating a small part of the organic solvent in the outermost of the catalyst pellet. The catalyst pellet was then impregnated, using the incipient wetness method, with a 1 mol/l aqueous solution of Pd(NO$_3$)$_2$. The resulting preparation was dried at 120° C. for 3 h and then calcined at 500° C. for 3 h, resulting in an eggshell-type pellet with a total noble metal content of 0.18 wt % the palladium situated in the 0.5% outermost volume of the catalyst.

The obtained catalysts were subject to investigation in the gas phase at various conditions. As it was already determined that the reaction was of a fast nature, the experiments were performed at a constant outer-surface-area load. The experiments were run at an aldehyde-to-hydrogen ratio of 1:2 on a molar basis and at 5 bar operating pressure.

Figure 1:
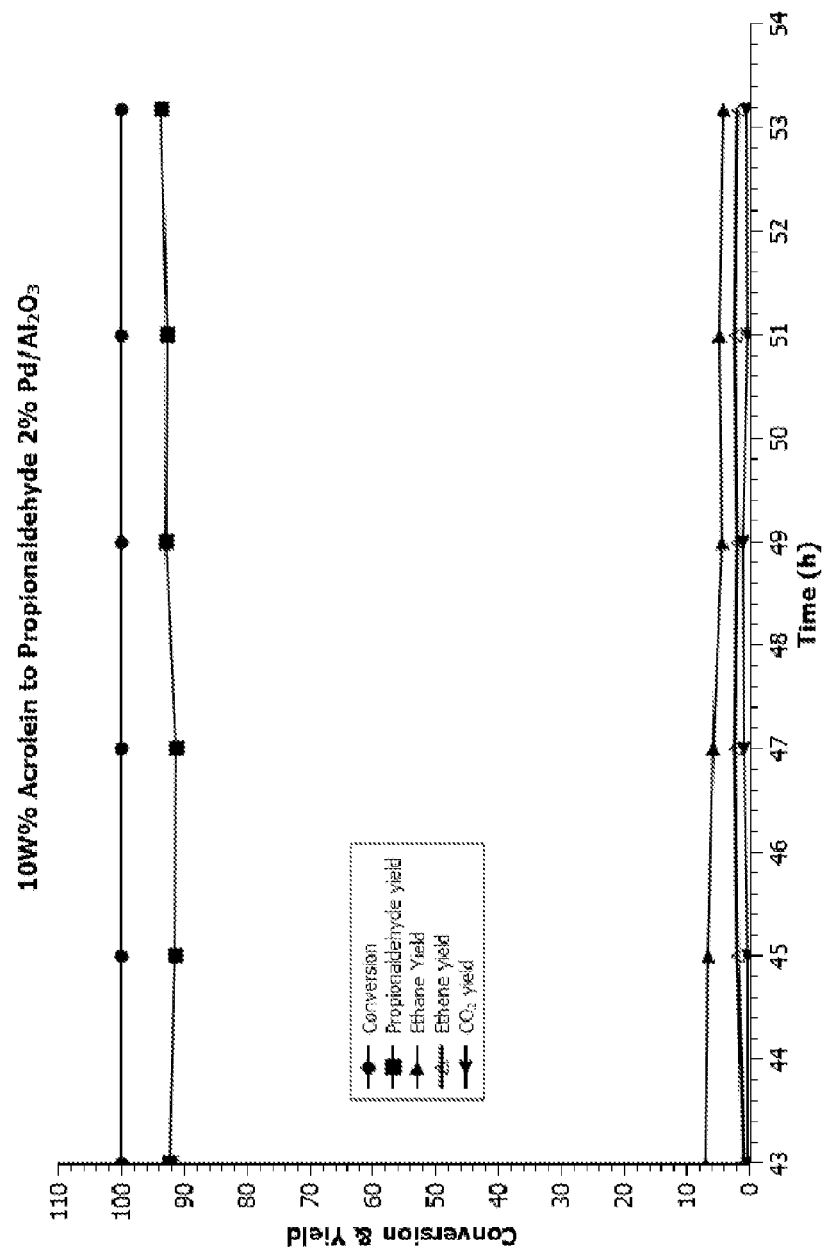
FIG. 1 depicts the results obtained with a homogeneous catalyst at 200° C. and 4 bar(g) pressure.

An aqueous solution of 10 wt % acrolein and hydrogen was fed to a pre-heater, wherein the mixture was heated to about 150° C. The resulting mixed gaseous stream was then fed to a reactor comprising the catalyst. The catalysts were run for a minimum of 40 hours on-stream. In FIG. 1, the results obtained with the homogeneous catalyst are depicted, while the results obtained with the egg-shell catalyst are depicted in FIG. 2.

Figure 2:
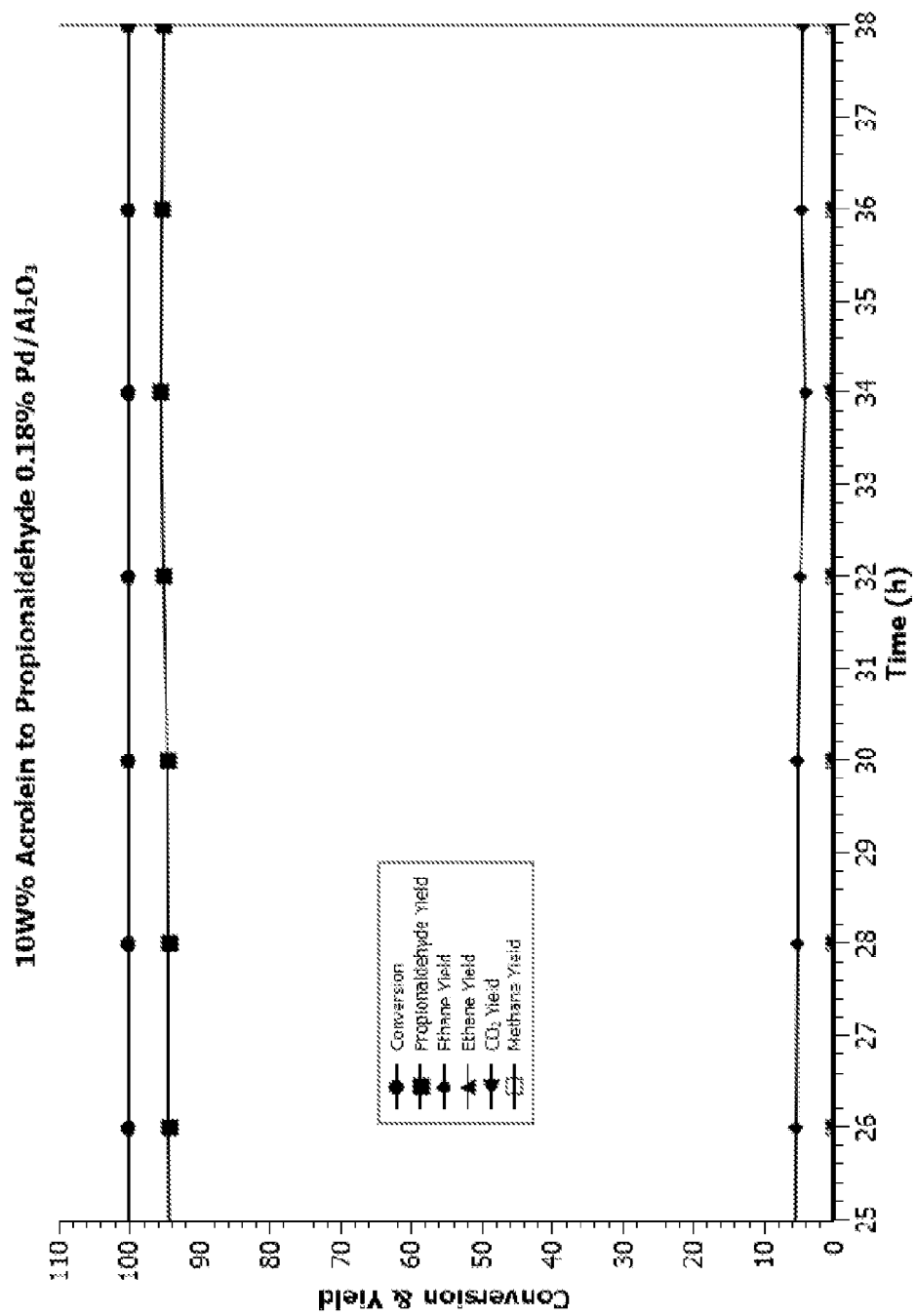
FIG. 2 depicts the results obtained with an egg-shell catalyst at 200° C. and 4 bar(g) pressure.
Figure 3:
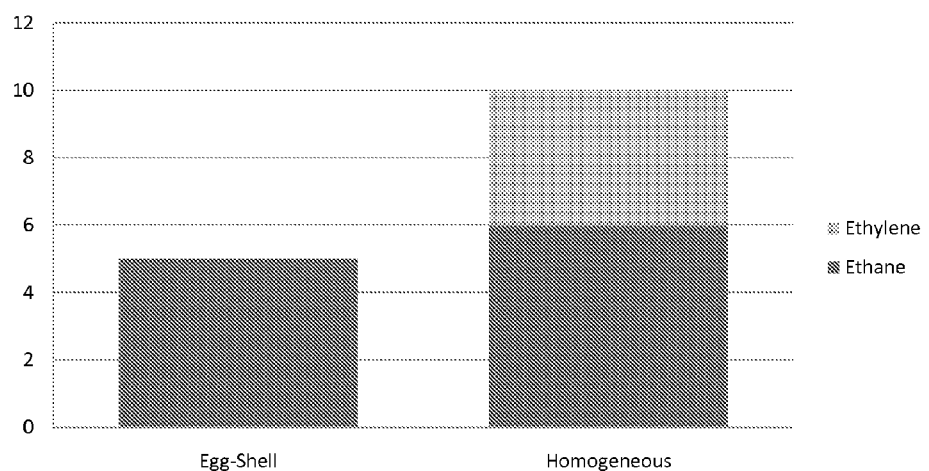
FIG. 3 depicts a comparison of the yield of side-products at 200° C. and 4 bar at constant surface-area load.

As seen from FIGS. 1 and 2, a constantly higher yield of propionaldehyde were obtained with the egg-shell catalyst. Further, the major by-products obtained with the homogenously prepared catalyst were ethane and ethylene (i.e. ethene). As is evident from FIG. 3, wherein the side-product formation is depicted, less ethane and no ethene were obtained as side-products with the egg-shell catalyst.

From the experiments, it stands clear that the egg-shell catalyst, comprising significantly less palladium, performs at least as well and most likely even better than the homogeneously prepared catalyst. Both catalysts may operate at high surface-area loadings, corresponding to 3 000 to 10 000 h$^{-1}$ on an industrial type set-up (larger diameter catalysts, 4-6 mm diameter). Further, as already elaborated the egg-shell catalyst give rise to less amount and number of side-products at the same temperature compared to the homogeneously impregnated catalyst. Therefore it seems likely that the egg-shell catalyst may operate at higher space velocities on an industrial scale.

The invention claimed is:

1. A method of hydrogenating a carbon-carbon double bond conjugated with a carbonyl carbon in an 1,2-unsaturated carbonylic compound in gas phase, comprising the step of:
   passing a gaseous stream comprising said 1,2-unsaturated carbonylic compound to be hydrogenated and hydrogen over a palladium catalyst comprising a carrier and palladium, wherein said catalyst has a heterogeneous distribution of palladium, palladium being concentrated to the outermost surface of the catalyst, which outermost surface is being exposed to the surrounding;
   wherein the temperature over said catalyst is 120 to 200° C. and the pressure over said catalyst is at least 0.1 MPa; and said 1,2-unsaturated carbonylic compound is an aldehyde according to structural formula (II),

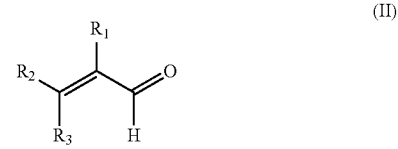

(II)

wherein R$_1$, R$_2$ and R$_3$, independently of each other, are selected from the group consisting of hydrogen and C$_{1-4}$ alkyl.

2. The method according to claim 1, wherein at least 95 wt % of the palladium in said catalyst is present at or within 1 mm of the outermost surface of said catalyst.

3. The method according to claim 1, wherein the catalyst is a particle or particles attached to each other, and at least 95 wt % of the palladium in the catalyst is present at the outermost surface of the catalyst, or within a distance from the outermost surface of the catalyst of not more than 1% of the distance between the outermost surface and the center of gravity of the particle.

4. The method according to claim 1, wherein at least 95.0 wt % of the palladium in the catalyst is concentrated to a skin periphery of the catalyst having a thickness not more than 400 μm.

5. The method according to claim 1, wherein the catalyst comprises not more than 1 wt % palladium.

6. The method according to claim 5, wherein the catalyst comprises at least 0.01 wt % palladium.

7. The method according to claim 1, wherein said carrier comprises alumina ($Al_2O_3$).

8. The method according to claim 7, wherein said carrier essentially consists of alumina ($Al_2O_3$).

9. The method according to claim 8, wherein the catalyst essentially consists of alumina and heterogeneously distributed palladium.

10. The method according to claim 7, wherein said alumina is alumina in the γ-form.

11. The method according to claim 1, wherein the temperature over said catalyst is 170 to 190° C.

12. The method according to claim 1, wherein the pressure over said catalyst is 0.1 to 10 MPa.

13. The method according to claim 1, wherein the molar amount of hydrogen in said gaseous stream is at least equal to the molar amount of 1,2-unsaturated carbonylic compound in said gaseous stream.

14. The method according to claim 13, wherein the molar amount of hydrogen 1 to 5 times the molar amount of 1,2-unsaturated carbonylic compound.

15. The method according to claim 1, wherein said gaseous stream further comprises steam.

16. The method according to claim 1, wherein said aldehyde is acrolein or crotonaldehyde.

17. The method according to claim 16, wherein said aldehyde is acrolein.

18. The method according to claim 1, wherein said method is performed in a reactor.

19. The method according to claim 18, wherein said reactor is a flow reactor.

* * * * *

UNITED STATES PATENT AND TRADEMARK OFFICE
CERTIFICATE OF CORRECTION

PATENT NO.        : 8,692,028 B2                                          Page 1 of 1
APPLICATION NO. : 13/517119
DATED             : April 8, 2014
INVENTOR(S)       : Hulteberg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 99 days.

Signed and Sealed this

Twenty-ninth Day of September, 2015

Michelle K. Lee
*Director of the United States Patent and Trademark Office*